United States Patent [19]

Clearfield et al.

[11] Patent Number: 4,512,905

[45] Date of Patent: Apr. 23, 1985

[54] METHOD OF MAKING SODIUM ZIRCONIUM SILICO-PHOSPHATES

[75] Inventors: Abraham Clearfield, College Station, Tex.; Paul Jerus, Louisville, Ky.

[73] Assignee: The Texas A&M University System, College Station, Tex.

[21] Appl. No.: 432,795

[22] Filed: Dec. 23, 1982

Related U.S. Application Data

[63] Continuation-in-part of Ser. No. 379,567, May 18, 1982, abandoned.

[51] Int. Cl.[3] .................... H01G 9/02

[52] U.S. Cl. .................... 252/62.2; 423/306; 429/104; 429/191; 429/193

[58] Field of Search .................... 423/306; 429/191, 193, 429/104, 33; 252/62.2

[56] References Cited

U.S. PATENT DOCUMENTS

| | | | |
|---|---|---|---|
| 4,049,891 | 9/1977 | Hong | 429/193 |
| 4,166,159 | 8/1979 | Pober | 429/193 |
| 4,394,280 | 7/1983 | von Alpen et al. | 429/104 |

FOREIGN PATENT DOCUMENTS

| | | | |
|---|---|---|---|
| 2052462 | 1/1981 | United Kingdom | 423/306 |

OTHER PUBLICATIONS

Bayard, M. L., "A Complex Impedance Analysis of the Ionic Conductivity of $Na_{l+x}Zr_2\ Si_x\ P_{3-x}O_{12}$ Ceramics", J. Electroanal. Chem. 91, (1978), pp. 201-209.

*Primary Examiner*—John Doll
*Assistant Examiner*—Jackson Leeds
*Attorney, Agent, or Firm*—Deane E. Keith; Forrest D. Stine

[57] ABSTRACT

Homogeneous sodium zirconium silico-phosphates having the formula $$Na_{1+x+4y}Zr_{2-y}(SiO_4)_x(PO_4)_{3-x}$$

where x is from 1 to 2.8 and y is between 0 and about 0.5, are prepared by heating a zirconium phosphate with an aqueous, alkaline sodium silicate solution and calcining the resulting solid orthorhombic crystalline product. The calcined product is useful as a solid electrolyte for transporting sodium ions in a sodium-sulfur storage battery.

9 Claims, No Drawings

METHOD OF MAKING SODIUM ZIRCONIUM SILICO-PHOSPHATES

This is a continuation-in-part of U.S. Ser. No. 379,567, filed May 18, 1982, now abandoned.

SUMMARY OF THE INVENTION

Sodium zirconium silico-phosphates having the formula $$Na_{1+x+4y}Zr_{2-y}(SiO_4)_x(PO_4)_{3-x}$$

where x is between about 1.0 and about 2.8 and y is between 0 and about 0.5, are prepared as pure, single-phase compositions in a multi-stage process which includes the hydrothermal preparation of a novel hydrated orthorhombic crystalline intermediate composition and the subsequent calcination of the orthorhombic material to form the pure, single-phase, crystalline product.

DESCRIPTION OF THE INVENTION

Storage batteries with the same energy and power as the conventional lead-lead oxide battery but much lighter in weight and much smaller in size can be made using liquid sodium and liquid sulfur as the negative and positive electrodes, together with a suitable solid electrolyte membrane separating the liquid electrodes. In order to function effectively as an electrolyte between the liquid electrodes, the solid membrane must have high sodium ion conductivity and low electronic conductivity, and must be chemically stable, both to the liquid sodium and to the liquid sulfur.

Hong et al. in Mat. Res. Bull. Vol. 11, pp. 173–182 and 203–220, 1976, and U.S. Pat. No. 4,049,891, have proposed a crystalline membrane for the sodium-sulfur cell formed from a sodium zirconium silico-phosphate having the formula:

$$Na_{1+x}Zr_2Si_xP_{3-x}O_{12}$$

where x is between about 0.4 and about 2.8. Hong et al., Mat. Res. Bull., Vol. 13, p. 757, 1978, call this material "Nasicon" for Sodium Superionic Conductor. These compositions were produced by heating powdered sodium carbonate, zirconia, silica and ammonium acid phosphate in stages to a final temperature of about 1200° C. over a period of time. The resulting powdered monoclinic or rhombohedral sodium zirconium silico-phosphate product was pressed into flat shapes which demonstrated good sodium ion transport properties. However, this method results in a product containing free zirconia which reduces the product's ionic conductivity, as pointed out by Bayard et al. in J. Electroanal. Chem., 91 (1978) 201–209.

Boilot et al., Mat. Res. Bull. Vol. 14, pp. 1469–1477, 1979, have proposed a different method for the preparation of the sodium zirconium silico-phosphates by using different initial reactants to make a gel intermediate which dries to an amorphous powder for subsequent calcination. Von Alpen et al., Solid State Ionics 3/4 (1981) pp. 215–218, North-Holland Publishing Company, postulate that sodium zirconium silico-phosphate conforming to the formula:

$$Na_{1+x}Zr_2Si_xP_{3-x}O_{12}$$

where x is from 0.4 to 2.8, i.e. Nasicon, cannot be produced as a pure monophase. However, Von Alpen et al. additionally demonstrate that certain single-phase compositions outside the ranges defined by this formula can be produced. Quon et al., Mat. Res. Bull., Vol. 15, pp. 1533–1539, 1980 have postulated that zirconia precipitates out of Nasicon as a result of sodium loss during high temperature calcination. When sintering was carried out in the presence of high soda vapor obtained from adjacent sodium aluminate, zirconia precipitation was substantially reduced.

We have discovered a multi-step process for preparing a homogeneous sodium zirconium silico-phosphate composition having fast sodium ion transport properties which has the formula:

$$Na_{1+x+4y}Zr_{2-y}Si_xP_{3-x}O_{12}$$

where x is between about 1.0 and about 2.8, preferably between about 1.8 and about 2.3, and y is between 0 and about 0.5. By "homogeneous" we mean that the sodium zirconium silico-phosphate is a single-phase crystalline product which does not contain a significant or detectable amount of any non-sodium zirconium silico-phosphate component, such as zirconia, dispersed or deposited within the crystal lattice. Such foreign material would reduce the ionic conductivity of the product by interfering with or blocking the migration of the sodium cation through the crystal lattice.

In our process, the various ions are permitted to combine in optimum ratios different from their relative concentration in the reaction solution to form a novel hydrated orthorhombic crystalline intermediate having the same general formula on a water-free basis as set out in the preceding paragraph. When calcined, this orthorhombic intermediate is converted to the desired homogeneous sodium zirconium silicophosphate having high ionic conductivity without producing a separate, detectable zirconia phase and without requiring an atmosphere of soda vapor during calcination. Our process involves, in its first stage, heating an aqueous solution containing sodium ion, silicate ion, and a suspension of a suitable zirconium phosphate for sufficient time to obtain sodium ion and silicate ion exchange within the zirconium phosphate. When appropriate conditions and proportions are used, the washed and dried precipitate produces a unique X-ray diffraction pattern, showing an orthorhombic cell.

In the second stage of our process the purified and dried orthorhombic material is heated at a temperature between about 1000° C. to about 1250° C. until it has been converted to the homogeneous sodium zirconium silico-phosphate fast ion conductor. At the lower temperatures within this temperature range, the conversion reaction tends to be quite slow, and at the higher temperatures decomposition of the desired product tends to occur. For this reason we prefer a calcination temperature within the range of about 1100° C. to about 1225° C.

As stated, one of the initial reactants is a zirconium phosphate. By this we mean to include that class of compounds having the formula $$Zr(MPO_4) \cdot zH_2O$$

where M is hydrogen, sodium, or a mixture of hydrogen and sodium and z is from 0 to 10. This formula includes:
α-zirconium phosphate, $Zr(HPO_4)_2 \cdot H_2O$;

γ-zirconium phosphate, $Zr(HPO_4)_2.2H_2O$;
sodium acid zirconium phosphate, $NaHZr(PO_4)_2$;
sodium zirconium phosphate, $Na_2Zr(PO_4)_2$; and the like.

The sodium and silica ions required in the solution can be obtained from a single compound, a suitable sodium silicate, or several compounds such as a sodium silicate and sodium hydroxide. A key to our process is the presence in the solution of a proper ratio of the sodium and silicate ions, in order to keep the silicate in solution. For convenience, we specify this ratio as the mol ratio of $Na_2O$ to $SiO_2$, that is, the soda to silica mol ratio. Thus the $Na_2O:SiO_2$ mol ratio in sodium orthosilicate, $Na_4SiO_4.2H_2O$ is 2:1, and the mol ratio in sodium metasilicate, $Na_2SiO_3.9H_2O$ is 1:1. For this purpose sodium hydroxide can be viewed as $Na_2O.H_2O$. In our process, the $Na_2O:SiO_2$ mol ratio in the reaction solution should be between about 0.9:1 and about 4:1, and preferably between about 1:1 and about 3:1 in order to carry out our process to the best advantage. This means that the solution will have a sufficiently high pH, such as at least about 10.0, to ensure that all of the silica is in solution, and it will include sufficient sodium to exchange with any hydrogen in the zirconium phosphate compound.

Also important to the successful reaction is the maintenance of a suitable silica to zirconium phosphate mol ratio. We have determined that the mol ratio of $SiO_2$ to the zirconium phosphate compound should broadly be within the range of between about 1:1 and about 2:1, and preferably within the range of between about 1.2:1 and about 1.8:1. When the relative proportions of soda, silica and zirconium phosphate are suitably proportioned, the desired homogeneous product can be obtained.

A special feature of our process further distinguishes it from prior procedures. In the prior art procedures, the relative proportion of the elements in the reaction mixture and in the product are the same. However, this is not true in our reaction. Thus, we utilize excess soda, silica and phosphate which is not incorporated in the final product. The relative excess amount of these components and the reaction conditions determine the nature and composition of the final product. When the reactants are suitably proportioned and the reaction conditions are suitably selected, the novel solid, orthorhombic intermediate product is obtained. The X-ray diffraction pattern of this orthorhombic material does not correspond to any known phosphate in the ASTM Powder Diffraction file.

The conditions which are particularly desirable for obtaining this orthorhombic product include a suitable reaction temperature and sufficient time to complete the reaction. The reaction temperature should desirably be at least about 250° C., preferably at least about 275° C. The maximum temperature will generally be about 350° C. and preferably it will be no higher than about 325° C. The reaction is advantageously carried out for at least about 1 hour up to about 100 hours, more preferably within the range of between about 2 and about 30 hours. Since time and temperature are inter-related, albeit inversely, the reaction time for the desired complete reaction, in part, is determined by the reaction temperature. Pressure is not critical to the success of the reaction but will generally be elevated since the reaction will generally be carried out in a closed vessel in order to avoid the loss of the aqueous phase at the elevated temperature required for reaction.

After the reaction is completed, the powdered orthorhombic product is filtered, washed and dried. It is then heated up to the calcination temperature for slow conversion to the monoclinic or rhombohedral ionic conducting form. The composition determines whether the product develops the monoclinic or the rhombohedral form, or a mixture of the two. When x in the above formula approaches 2.0, the monoclinic form tends to develop, while the rhomobohedral form tends to prevail as x moves away from the vicinity of 2.0. The mono-clinic crystalline form is preferred because it possesses greater ionic conductivity and is more resistant to degradation under thermal shock.

DESCRIPTION OF PREFERRED EMBODIMENTS

Example 1

A solution was prepared containing 1.84 g (0.01 mol) of $Na_4SiO_4$ in about 40 ml of water. To this solution was added approximately 2 g (0.0066 mol) of α-zirconium phosphate. This mixture was transferred to a closed teflon-lined reactor vessel and heated at 300° C. for 20 hours. The pressure was estimated to be from about 100 to about 120 atmospheres. At the completion of the reaction the powdered solid product was recovered by filtration, then washed and dried. The X-ray pattern for this material was as follows:

| d(Å) | 6.07 | 4.98 | 4.50 | 4.38 | 3.85 | 3.77 | 3.55 | 3.36 |
|---|---|---|---|---|---|---|---|---|
| I/Io | 60 | 100 | 10 | 15 | 30 | 30 | 40 | 5 |
| d(Å) | 3.23 | 3.13 | 3.03 | 2.81 | 2.63 | 2.55 | | |
| I/Io | 8 | 20 | 8 | 90 | 20 | 35 | | |

The product could be indexed on the basis of an orthorhombic cell with cell dimensions:
a = 8.743 Å,
b = 10.587 Å, and
c = 7.317 Å

On heating at 1200° C. for 3 to 4 hours, the material converted completely to Nasicon as determined from the published X-ray data. No trace of zirconia was identified in the X-ray pattern. Its unit cell dimensions were determined to be:
a = 15.609 Å,
b = 9.023 Å,
c = 9.215 Å, and
β = 123.98°.

Example 2

A 12.8 g (0.32 mol) portion of sodium hydroxide was dissolved in 500 ml of water (0.64M) and 19.5 g (0.16 mol) of sodium metasilicate, $Na_2SiO_3$, was dissolved in this alkaline solution. This was followed by the addition of 30.2 g (0.1 mol) of powdered α-zirconium phosphate, $Zr(HPO_4)_2.H_2O$, which was dispersed throughout the solution with stirring. The mixture was transferred to a telfon-lined pressure reactor which was filled to the 50-percent level. The reactor contents were treated at 275°–285° C. for 20 hours. Completion of reaction was indicated by the following X-ray pattern for the recovered solid orthorhombic material:

| d(Å) | 6.07 | 5.02 | 4.50 | 4.38 | 3.86 | 3.77 | 3.56 | 3.38 |
|---|---|---|---|---|---|---|---|---|
| I/Io | 66 | 88 | 15 | 22 | 31 | 31 | 31 | 5 |

| d(Å) | 3.24 | 3.18 | 2.88 | 2.64 | 2.56 |
|---|---|---|---|---|---|
| I/Io | 5 | 33 | 100 | 22 | 33 |

Analysis of this orthorhombic crystalline material showed 13.89 percent sodium, 29.87 percent zirconium, 3.57 percent phosphorus, 10.25 percent silicon, 6.66 percent water. After the solid was heated at 1150°–1200° C. for about 10 hours, it provided the following X-ray pattern which identified it as Nasicon:

| d(Å) | 6.51 | 6.47 | 4.658 | 4.609 | 4.519 | 4.505 | 3.597 | 3.904 | 3.885 |
|---|---|---|---|---|---|---|---|---|---|
| I/Io | 45 | 43 | 82 | 60 | 100 | 100 | 38 | 38 | 40 |
| d(Å) | 3.869 | 3.682 | 3.250 | 3.223 | 2.939 | 2.925 | 2.906 | 2.632 | 2.603 |
| I/Io | 35 | 4 | 27 | 60 | 60 | 70 | 50 | 23 | 50 |

No impurity such as zirconia was identified in the X-ray pattern. By elemental analysis, this calcined product was found to contain 14.06 percent sodium, 29.83 percent zirconium, 3.72 percent phosphorus, and 9.66 percent silicon.

Another powdered product prepared by this procedure was compressed to a solid disk, about 4 mm thick and about 21 mm in diameter, to a solid having a density of about 92 percent of theoretical. Its electrical conductance, which was measured in a vector-impedance meter (5 Hz to 500 kHz) made by Hewlett-Packard, Model 4800A, was found to be 0.115 ohm$^{-1}$cm$^{-1}$ at 300° C.

This compressed solid product can be used in the form of a membrane as a solid electrolyte for the transport of sodium ion in chemical sensors, solid-state displays, storage batteries of the sodium-sulfur type, and the like.

It is to be understood that the above disclosure is by way of specific example and that numerous modifications and variations are available to those of ordinary skill in the art without departing from the true spirit and scope of the invention.

We claim:

1. A method of preparing a crystalline compound which provides fast sodium ion transport which comprises heating a hydrated orthorhombic crystalline solid having the formula on a water-free basis

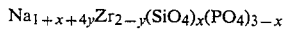

where x is between about 1.0 and about 2.8 and y is between 0 and 0.5, at a temperature between about 1,000° C. and about 1,250° C. until the orthorhombic crystalline solid is converted to a homogeneous, fast sodium ion conducting, monoclinic or rhombohedral crystalline sodium zirconium silico-phosphate of the formula indicated above, or a mixture of the two free from any separate, detectable zirconia phase.

2. A method of preparing a crystalline compound which provides fast sodium ion transport in accordance with claim 1 in which x is between about 1.8 and about 2.3.

3. A method of preparing a crystalline compound which provides fast sodium ion transport in accordance with claim 1 which comprises heating the orthorhombic crystalline solid at a temperature between about 1,100° C. and about 1,225° C.

4. A method of preparing a crystalline compound which provides fast sodium ion transport and having the formula:

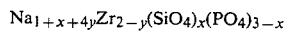

where x is between about 1.0 and about 2.8 and y is between 0 and 0.5, which comprises the steps:
heating an aqueous dispersion comprising soda and silica in solution in a mol ratio of soda to silica of between about 0.9:1 and about 4:1 and a powdered zirconium phosphate having the formula $Zr(MPO_4)_2 \cdot zH_2O$ where M is hydrogen, sodium or a mixture of hydrogen and sodium, and z is an integer from 0 to 10, in an amount to provide a mol ratio of silica to zirconium phosphate of between about 1.2:1 and about 1.8:1, the proportions of the soda, silica and phosphate in the reaction mixture being in excess of the proportions of these materials in the final product, said heating being conducted at a temperature between about 250° C. and about 350° C., until reaction occurs and a precipitate is formed,
separating precipitated material from supernatant liquid, and washing and drying such separated precipitate to recover a hydrated orthorhombic crystalline solid, and
calcining the hydrated orthorhombic crystalline solid at a temperature between about 1000° C. and about 1250° C. until conversion to a homogeneous, fast sodium ion conducting, monoclinic or rhombohedral crystalline, sodium zirconium silico-phosphate of the formula indicated above, or a mixture of the two, free from any separate, detectable zirconia phase, is substantially complete.

5. A method of preparing a crystalline compound which provides fast sodium ion transport in accordance with claim 4 in which the mol ratio of soda to silica is between about 1:1 and about 3:1.

6. A method of preparing a crystalline compound which provides fast sodium ion transport in accordance with claim 4 in which the aqueous dispersion is heated at a temperature between about 275° C. and about 325° C.

7. A method of preparing a crystalline compound which provides fast sodium ion transport in accordance with claim 4 in which the solid product is calcined at a temperature between about 1,100° C. and about 1,225° C.

8. A method of preparing a crystalline compound which provides fast sodium ion transport in accordance with claim 4 in which M is hydrogen.

9. A method of preparing a crystalline compound in accordance with claim 4 in which x is between about 1.8 and about 2.3.

* * * * *